(12) United States Patent
Crawford et al.

(10) Patent No.: US 10,806,936 B2
(45) Date of Patent: Oct. 20, 2020

(54) COCHLEAR IMPLANTS AND MAGNETS FOR USE WITH SAME

(71) Applicant: ADVANCED BIONICS AG, Staefa (CH)

(72) Inventors: Scott A. Crawford, Castaic, CA (US); James George Elcoate Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 14 days.

(21) Appl. No.: 15/770,207

(22) PCT Filed: Nov. 20, 2015

(86) PCT No.: PCT/US2015/062015
§ 371 (c)(1),
(2) Date: Apr. 22, 2018

(87) PCT Pub. No.: WO2017/087004
PCT Pub. Date: May 26, 2017

(65) Prior Publication Data
US 2018/0304078 A1   Oct. 25, 2018

(51) Int. Cl.
*A61N 1/375* (2006.01)
*A61N 1/05* (2006.01)
*A61N 1/36* (2006.01)
*A61N 1/372* (2006.01)
*H04R 25/00* (2006.01)

(52) U.S. Cl.
CPC ......... *A61N 1/3758* (2013.01); *A61N 1/0541* (2013.01); *A61N 1/36038* (2017.08); *A61N 1/37217* (2013.01); *H04R 25/606* (2013.01); *H04R 2225/67* (2013.01)

(58) Field of Classification Search
CPC .............. A61N 1/0541; A61N 1/36038; A61N 1/36142; A61N 1/3718
See application file for complete search history.

(56) References Cited

U.S. PATENT DOCUMENTS

| | | | |
|---|---|---|---|
| 4,352,960 | A | 10/1982 | Dormer et al. |
| 4,595,390 | A | 6/1986 | Hakim et al. |
| 4,606,329 | A | 8/1986 | Hough |
| 4,618,949 | A | 10/1986 | Lister |
| RE32,947 | E | 6/1989 | Dormer et al. |
| 5,290,281 | A | 3/1994 | Tschakaloff |

(Continued)

FOREIGN PATENT DOCUMENTS

| | | |
|---|---|---|
| EP | 2117489 B1 | 5/2010 |
| EP | 2853287 A1 | 4/2015 |

(Continued)

OTHER PUBLICATIONS

U.S. Appl. No. 15/568,469, filed Oct. 21, 2017, 20180110985A1.

(Continued)

*Primary Examiner* — Allen Porter
(74) *Attorney, Agent, or Firm* — Henricks Slavin LLP (57) ABSTRACT

A cochlear including a cochlear lead, a housing including a magnet pocket and a magnet aperture, a magnet, located within the magnet pocket, having a top surface adjacent to the magnet aperture that defines a top magnet outer perimeter and a bottom surface adjacent to the bottom wall that defines a bottom magnet outer perimeter that is greater than the top magnet outer perimeter, an antenna within the housing, a stimulation processor within the housing.

7 Claims, 5 Drawing Sheets

(56) References Cited

U.S. PATENT DOCUMENTS

| | | |
|---|---|---|
| 5,755,762 A | 5/1998 | Bush |
| 5,824,022 A | 10/1998 | Zilberman et al. |
| 5,945,762 A | 8/1999 | Chen et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 2004/0012470 A1 | 1/2004 | Zimmerling et al. |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0103350 A1 | 5/2008 | Farone |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1 | 11/2012 | Ball |
| 2013/0079749 A1 | 3/2013 | Overstreet et al. |
| 2013/0184804 A1 | 7/2013 | Dalton |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0100109 A1 | 4/2015 | Feldman et al. |
| 2015/0265842 A1 | 9/2015 | Ridker |
| 2015/0367126 A1 | 12/2015 | Smyth |
| 2015/0382114 A1 | 12/2015 | Andersson et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2018/0028818 A1 | 2/2018 | Andersson et al. |
| 2018/0110985 A1 | 4/2018 | Walter |
| 2018/0110986 A1 | 4/2018 | Lee |
| 2018/0133486 A1 | 5/2018 | Smith |
| 2018/0185634 A1 | 7/2018 | Smyth |
| 2018/0296826 A1 | 10/2018 | Lee et al. |
| 2018/0369586 A1 | 12/2018 | Lee et al. |
| 2019/0046797 A1 | 2/2019 | Calixto et al. |
| 2019/0076649 A1 | 3/2019 | Lee et al. |

FOREIGN PATENT DOCUMENTS

| | | |
|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |

(56) References Cited

FOREIGN PATENT DOCUMENTS

| WO | WO2017105604 A1 | 6/2017 |
|----|-----------------|--------|
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |

OTHER PUBLICATIONS

U.S. Appl. No. 16/060,383, filed Jun. 7, 2018, 20180369586 A1.
U.S. Appl. No. 15/591,054, filed May 9, 2017, U.S. Pat. No. 9,919,154.
U.S. Appl. No. 16/009,600, filed Jun. 15, 2018, 20180296826A1.
U.S. Appl. No. 15/568,470, filed Oct. 21, 2017, 20180110986A1.
U.S. Appl. No. 16/101,390, file Aug. 10, 2018, 20190046797 A1.
U.S. Appl. No. 15/703,808, filed Sep. 13, 2017.
U.S. Appl. No. 15/805,025, filed Nov. 6, 2017, 20180133486 A1.
Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imaging and Cochlear Implants: Compatibility and Safety Aspects," Journal of Magnetic Resonance Imaging, Society for Magnetic Resonance Imaging, vol. 9, No. 1, pp. 26-38, Jan. 1, 1999.
PCT International Search and Written Opinion dated Jul. 22, 2016 for PCT App. Ser. No. PCT/US2015/062015.
U.S. Appl. No. 16/403,582, filed May 5, 2019.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 15/703,808, filed Sep. 13, 2017, 20190076649 A1.

COCHLEAR IMPLANTS AND MAGNETS FOR USE WITH SAME

CROSS-REFERENCE TO RELATED APPLICATIONS

This application is the U.S. National Stage of PCT App. Ser. No. PCT/US2015/062015, filed Nov. 20, 2015.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

Figures 1, 2A:
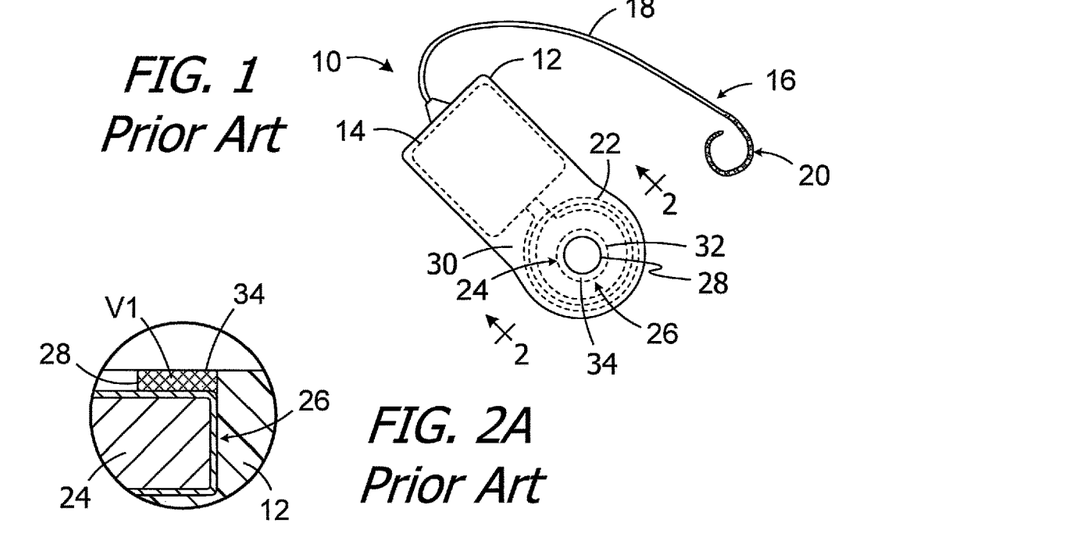
FIG. 1 is a plan view of a conventional cochlear implant.
FIG. 2A is an enlarged view of a portion of FIG. 2.
Figure 2:
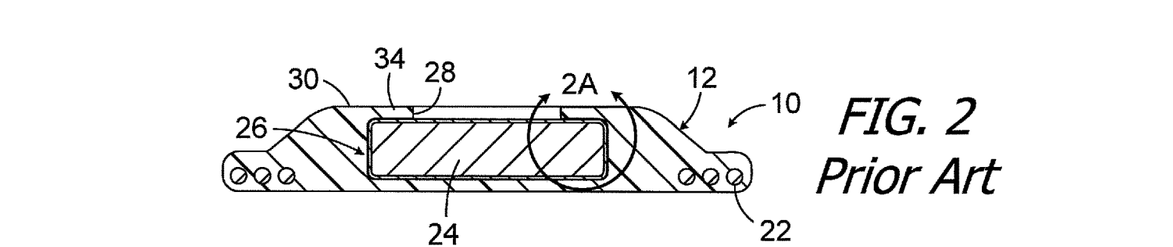
FIG. 2 is a section view taken along line 2-2 in FIG. 1.

One example of a conventional cochlear implant (or "implantable cochlear stimulator") is the cochlear implant 10 illustrated in FIGS. 1 and 2. The cochlear implant 10 includes a flexible housing 12 formed from a silicone elastomer or other suitable material, a processor assembly 14, a cochlear lead 16 with a flexible body 18 and an electrode array 20, and an antenna 22 that may be used to receive data and power by way of an external antenna that is associated with, for example, a sound processor unit. A cylindrical positioning magnet 24, with north and south magnetic dipoles that are aligned in the axial direction of the disk, is located within the housing 12. The magnet 24 is used to maintain the position of a headpiece transmitter over the antenna 22.

It is sometimes necessary to remove the magnet from the cochlear implant, and then reinsert the magnet, in situ, i.e., with the cochlear implant accessed by way of an incision in the skin. To that end, the positioning magnet 24 is carried within an internal magnet pocket 26 and can be inserted into, and removed from, the housing pocket by way of a magnet aperture 28 that extends through the housing top wall 30. The magnet 22 is larger than the magnet aperture 28, i.e., the outer perimeter of the magnet is greater than the perimeter of the magnet aperture. The portion of the top wall 30 between the aperture 28 and the outer edge 32 of the magnet 24 forms a retainer 34 that, absent deformation of the aperture and retainer, prevents the magnet from coming out of the housing 12. The volume V1 of the ring of housing material that forms the retainer 34 (which is the same flexible material that forms the remainder of the housing 12) is shown with cross-hatching in the cross-section illustrated in FIG. 2A. During installation and removal, the aperture 28 and retainer 34 are stretched or otherwise deformed so that the magnet 24 can pass through the aperture 28.

Figure 3:
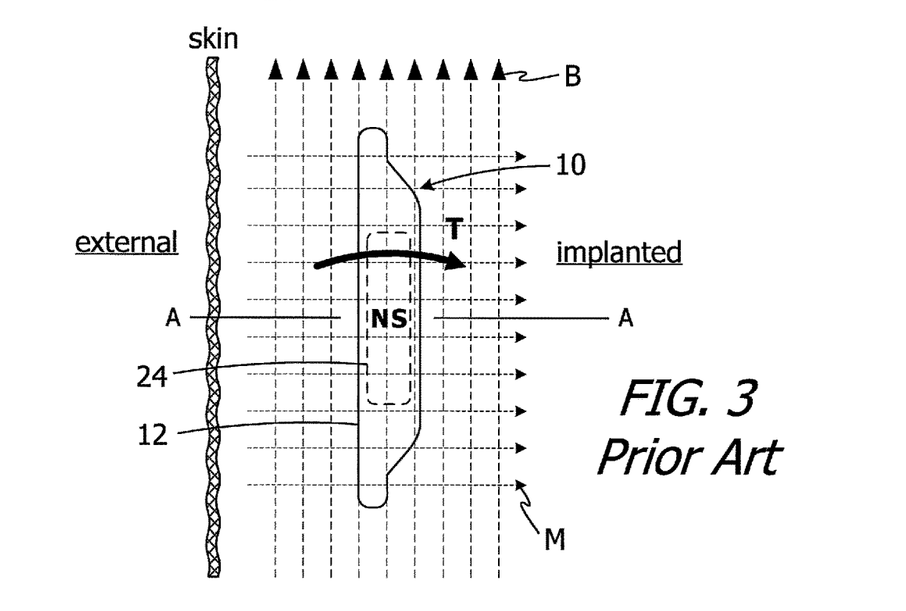
FIG. 3 is a side view showing a conventional cochlear implant in an MRI magnetic field.

The present inventors have determined that conventional cochlear implants are susceptible to improvement. For example, some conventional cochlear implants may not be compatible with magnetic resonance imaging ("MRI") systems. As illustrated in FIG. 3, the implant magnet 24 produces a magnetic field M in a direction that is perpendicular to the patient's skin and parallel to the axis A. This magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may generate a significant amount of torque T on the implant magnet 24. The torque T may be sufficient to deform the retainer 34 and dislodge the implant magnet 24 from the pocket 26 by way of the aperture 28 and/or reverse the magnet. In particular, the present inventors have determined that the volume V1 of flexible housing material that forms the retainer 34 can be insufficient to resist the torque T on the implant magnet 24.

One proposed solution involves surgically removing the implant magnet 24 prior to an MRI procedure and then surgically replacing the implant magnet thereafter. The present inventors have determined that a solution which allows an MRI procedure to be performed without magnet removal/replacement surgery, but which also permits magnet removal/replacement if otherwise necessary, would be desirable.

SUMMARY

A cochlear implant in accordance with one of the present inventions includes a cochlear lead, a housing including a magnet pocket and a magnet aperture, a magnet, located within the magnet pocket, having a top surface adjacent to the magnet aperture that defines a top magnet outer perimeter and a bottom surface adjacent to the bottom wall that defines a bottom magnet outer perimeter that is greater than the top magnet outer perimeter, an antenna within the housing, a stimulation processor within the housing. The present inventions also include systems with such a cochlear implant in combination with a headpiece.

A cochlear implant in accordance with one of the present inventions includes a cochlear lead, a flexible housing formed from a first flexible material having a first hardness and including a magnet pocket and a magnet aperture, a magnet with a side surface within the magnet pocket, a flexible buttress located within the flexible housing and adjacent to the side surface of the magnet, the flexible buttress being formed from a second flexible material having a second hardness that is greater than the first hardness, an antenna within the housing, a stimulation processor within the housing. The present inventions also include systems with such a cochlear implant in combination with a headpiece.

There are a number of advantages associated with such apparatus. For example, the torque applied to the implant magnet by a strong magnetic field, such as an MRI magnetic field, will not dislodge the implant magnet from the within the housing and/or reverse the magnet. As a result, surgical removal of the cochlear implant magnet prior to an MRI procedure, and then surgical replacement thereafter, is not required. In those instances where removal is required, the present cochlear implants need not preclude such removal and replacement. Additionally, the present cochlear implants prevent the implant magnet from being dislodged and/or reversed without increasing the thickness and volume of the implant or substantially increasing the rigidity of the implant.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 4:
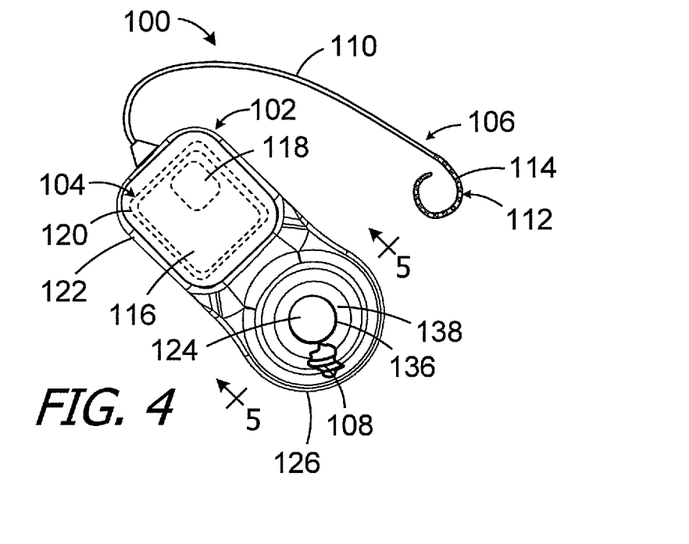
FIG. 4 is a plan view of a cochlear implant in accordance with one embodiment of a present invention.

One example of a cochlear implant (or "implantable cochlear stimulator") in accordance with the present inventions is the cochlear implant 100 illustrated in FIGS. 4-8. Referring first to FIG. 4, the exemplary cochlear implant 100 includes a resilient flexible housing 102 formed from a silicone elastomer or other suitable material, a processor assembly 104, a cochlear lead 106, and an antenna 108 that may be used to receive data and power by way of an external antenna that is associated with, for example, a sound processor unit. The cochlear lead 106 may include a flexible body 110, an electrode array 112 at one end of the flexible body 102, and a plurality of wires (not shown) that extend through the flexible body from the electrodes 114 (e.g., platinum electrodes) in the array 112 to the other end of the flexible body. The exemplary antenna 108 is a coil antenna with one or more loops (or "turns"), and three loops are shown in the illustrated embodiment. The exemplary processor assembly 104, which is connected to the electrode array 112 and antenna 108, includes a printed circuit board 116 with a stimulation processor 118 that is located within a hermetically sealed case 120. The stimulation processor 118 converts stimulation data into stimulation signals that stimulate the electrodes 114 of the electrode array 112. The hermetically sealed case 120 is located within a processor portion 122 of the housing 102. A positioning magnet 124 is located within an antenna portion 126 of the housing 102. The magnet 124, which is used to maintain the position of a headpiece transmitter over the antenna 108, is centered relative to the antenna 108.

Figure 5:
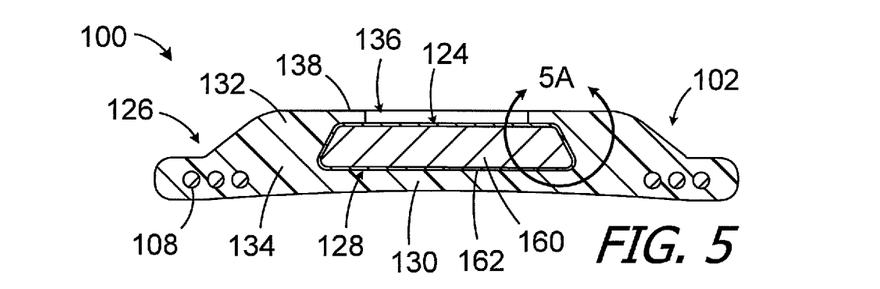
FIG. 5 is a section view taken along line 5-5 in FIG. 4.

Turning to FIG. 5, the exemplary housing antenna portion 126 includes a magnet pocket 128 which is surrounded by a bottom wall 130 that is located under the magnet pocket (in the illustrated orientation), a top wall 132 that is located above the magnet pocket (in the illustrated orientation) and a side wall 134 that is lateral of, and extends around, the magnet pocket. During use, the housing bottom wall 130 faces the patient's skull and the outer surface of the bottom wall defines a portion of the bottom surface of the cochlear implant 100, which is the surface of the cochlear implant that faces the patient's skull. The magnet 124 can be inserted into, and removed from, the magnet pocket 128 by way of a magnet aperture 136 that extends through the housing top wall 132. The magnet 124 is larger than the magnet aperture 136 and portions of the top wall 132 and side wall 134 between the magnet aperture 136 and the side surface of the magnet 124 form a retainer 138.

As the strength of a conventional retainer (e.g., retainer 34 in FIG. 2) may be insufficient to prevent a conventional magnet from being dislodged during an MRI procedure, the present implant housing 102 and magnet 124 are configured so as to increase the volume of material that defines the retainer 138, as compared to the conventional retainer in an otherwise identical cochlear implant, without increasing the thickness and volume of the implant. To that end, and referring to FIGS. 6-8, the exemplary magnet 124 has a top surface 140, a bottom surface 142, and a side surface 144 between the top and bottom surfaces. The perimeter $P_{MT}$ of the top surface 140 is less than the perimeter $P_{MB}$ of the bottom surface 142. In the illustrated implementation, the magnet 124 has a frustoconical shape and, accordingly, the top and bottom surface perimeters $P_{MT}$ and $P_{MB}$ are circular and the diameter $D_{MT}$ of the top surface 140 is less than the diameter $D_{MB}$ of the bottom surface 142. The top and bottom corners (or "edges") 146 and 148 of the exemplary magnet 124 are rounded such that the cross-section is substantially trapezoidal (i.e., trapezoidal but for the rounded corners). The rounded edges ease insertion and removal of the magnet 124 to and from the pocket 128. The exemplary magnet pocket 128 (FIG. 8), which is similarly shaped, has a top surface 150, a bottom surface 152, a side surface 154 between the top and bottom surfaces, and rounded top and bottom corners 156 and 158. Here too, the perimeter of the top surface 150 is less than the perimeter of the bottom surface 152 and, in the illustrated implementation, the magnet pocket 128 has a frustoconical shape. The top and bottom surface perimeters of the magnet pocket 128 are, therefore, circular and the diameter $D_{PT}$ of the pocket top surface 150 is less than the diameter $D_{PB}$ of the bottom surface 122.

Figure 5A:
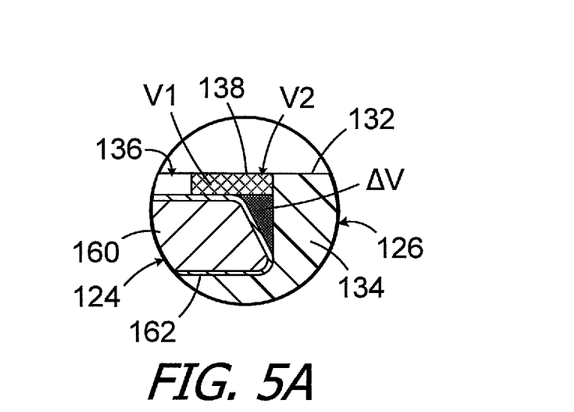
FIG. 5A is an enlarged view of a portion of FIG. 5.
Figure 6:
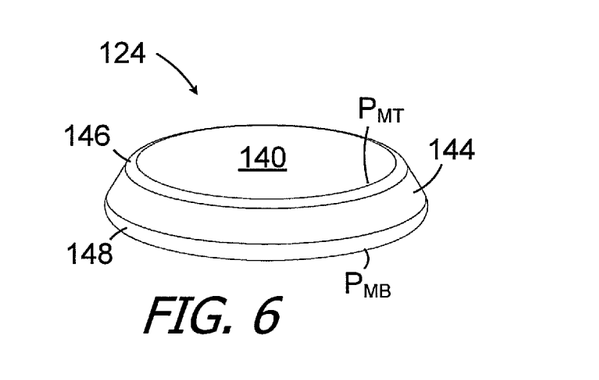
FIG. 6 is a perspective view of a magnet in accordance with one embodiment of a present invention.
Figure 7:
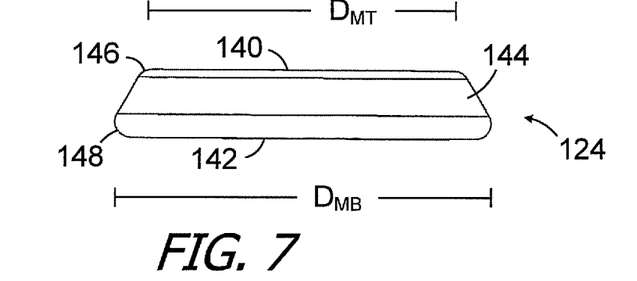
FIG. 7 is a side view of the magnet illustrated in FIG. 6.
Figure 8:
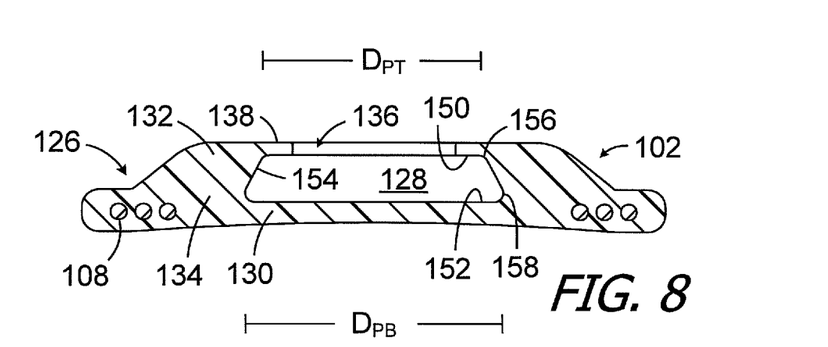
FIG. 8 is the section view illustrated in FIG. 5 with the magnet removed.

Turing to FIG. 5A, and as compared to the retainer 34, an additional volume ΔV of material is added to the volume V1 to form the volume V2 that defines the retainer 138. The material in the volume V2, which is the same flexible material that forms the remainder of the housing 102, is shown with both cross-hatching (volume V1) and gray (volume ΔV) in the cross-section illustrated in FIG. 5A. In the illustrated implementation, the respective configurations of the magnet 124 and the housing pocket 128 results in a retainer material volumetric increase of about 45%, as compared to an otherwise identical implant with a cylindrical magnet in a cylindrical pocket (e.g., the magnet 24 in pocket 26) having a diameter equal to the bottom surface diameter of the magnet 124, without increasing the volume or thickness of the implant. The torque generated by an MRI magnetic field will not dislodge the magnet 124 from the housing 102 and/or reverse the magnet within the housing in the manner described above with reference to FIGS. 1-3. Nevertheless, if necessary, the flexibility of the housing material allows the magnet 124 may be removed and replaced in situ. One example of a tool that may be used to remove the magnet 124, and then replace the magnet, is disclosed in PCT Pub. No. WO2014/164023.

Although the present inventions are not so limited, the exemplary magnet 124 includes a magnetic element 160 (FIGS. 5 and 5A) or magnetic object of some other shape formed from a ferromagnetic material and a thin hermetically sealed housing 162 formed from, for example, biocompatible metals and/or plastics. Such housing materials may, in some instances, be non-magnetic or paramagnetic. Suitable materials include, but are not limited to, titanium or titanium alloys, polyether ether ketone (PEEK), low-density polyethylene (LDPE), high-density polyethylene (HDPE) and polyamide. In particular, exemplary metals include commercially pure titanium (e.g., Grade 2) and the titanium alloy Ti-6Al-4V (Grade 5). With respect to size and shape, and although the present inventions are not so limited, in some implementations, the bottom magnet diameter $D_{MB}$ may range from 9 mm to 16 mm, the top magnet diameter $D_{MT}$ may range from 6 mm to 12 mm, and the thickness may range from 1.5 mm to 3.5 mm. The bottom magnet diameter $D_{MB}$ of the exemplary magnet 124 is 13.0 mm, the top magnet diameter $D_{MT}$ is 10.5 mm, and the thickness is 2.2 mm, in the illustrated embodiment. It should be noted, however, that magnet size is a function of the strength of the ferromagnetic material and, as stronger materials become available, the size may be reduced. The dimensions of the magnet pocket 128 may be equal to those of the magnet 124.

Figure 9:
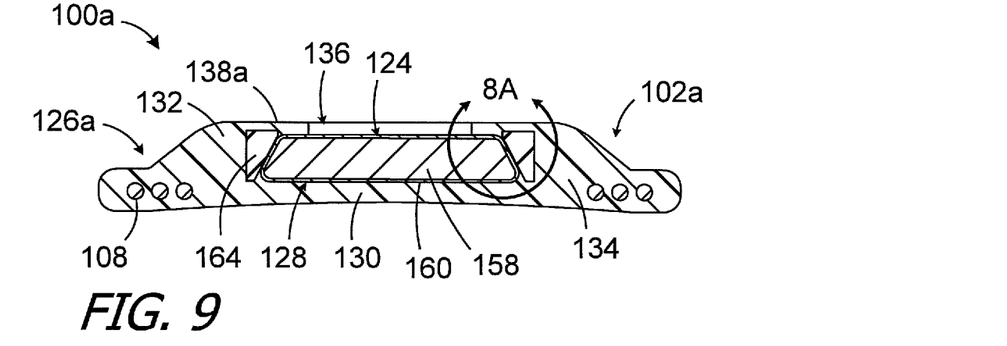
FIG. 9 is a section view of a cochlear implant in accordance with one embodiment of a present invention.
Figure 9A:
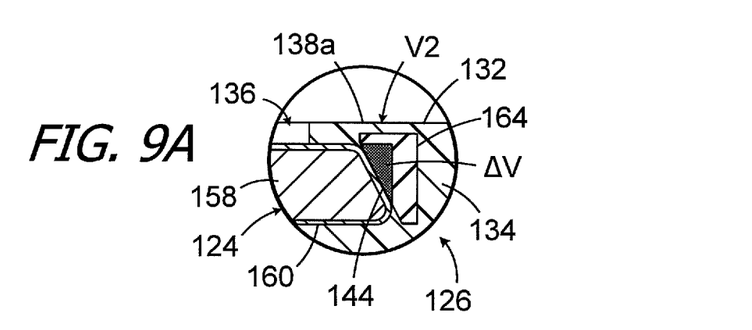
FIG. 9A is an enlarged view of a portion of FIG. 9.
Figure 10:
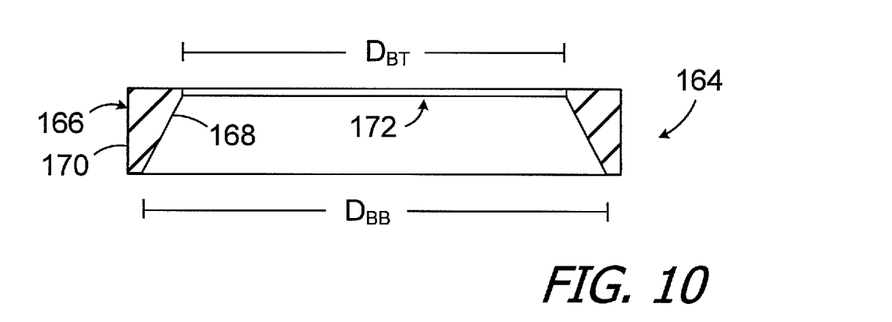
FIG. 10 is a section view of a flexible magnet buttress in accordance with one embodiment of a present invention.
Figure 11:
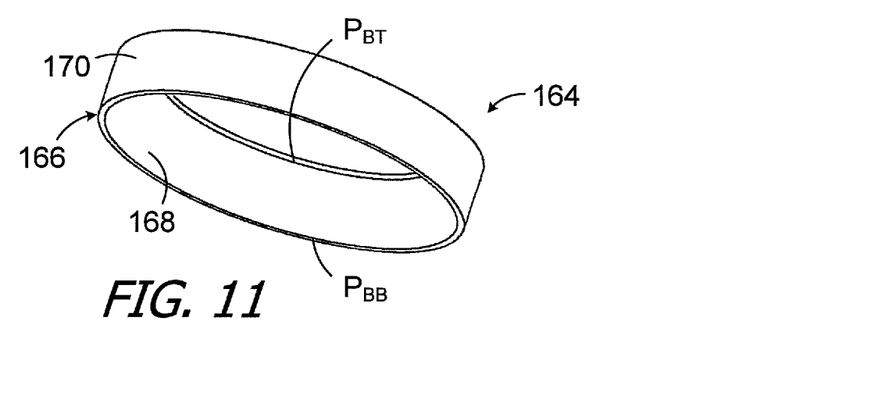
FIG. 11 is a perspective view of the flexible magnet buttress illustrated in FIG. 10.

Another exemplary cochlear implant is generally represented by reference numeral 100 in FIGS. 9 and 9A. Cochlear implant 100a is substantially similar to cochlear implant 100 and similar elements are represented by similar reference numerals. Here, however, a portion of the material that forms the retainer is harder than the material that forms the remainder of the housing, thereby increasing the strength of the retainer. By way of example, but not limitation, the exemplary housing 102a includes antenna portion 126a with a buttress 164 that is adjacent to (and in some instances is in contact with) the magnet side wall 144. The buttress 164 is formed from flexible material that is harder than the material that forms the remainder of the housing 102a. The buttress 164 forms part of the retainer 138a and, as a result, the retainer 138a is stiffer than the retainer 138. Turning to FIGS. 10 and 11, the buttress 164 includes a generally annular body 166 with an inner surface 168 having a size and shape that corresponds to the size and shape of the magnet side wall 144. The perimeter $P_{BT}$ and diameter $D_{BT}$ at the top of the inner surface 168 are equal to (or are close to equal to) the perimeter $P_{MT}$ and the diameter $D_{MT}$ of the magnet top 140, and the perimeter $P_{BB}$ and diameter $D_{BB}$ of the bottom of the inner surface 168 are equal to (or are close to equal to) the perimeter $P_{MB}$ and the diameter $D_{MB}$ of the magnet bottom 144. The buttress annular body 166 also has outer surface 170 as well as an opening 172 that is adjacent to the magnet aperture 136 and through which the magnet 124 can pass when a tool is used to remove and/or replace the magnet in the manner described in, for example, PCT Pub. No. WO2014/164023.

The volume of the buttress 164 may be larger than the volume ΔV created by the configurations of the magnet 124 and magnet pocket 128 (which is shown in gray in FIG. 9A), may be the same as the volume ΔV, or may be less than the volume ΔV. In the illustrated implementation, the volume of the buttress 164 is greater than the volume ΔV, and the additional buttress volume further strengthens the area around the magnet pocket 128. With respect to materials, the buttress 164 may be formed from a silicone elastomer or other suitable flexible material that is harder than the material that forms the remainder of the housing, yet still allows the housing 102a to conform to the skull and the magnet to be removed if necessary. In some instances, the buttress material may be from 27% to 63% harder than the housing material. For example, the buttress material may have a hardness that ranges from 70 to 90 Shore A, while the housing material may have a hardness that ranges from 55 to 70 Shore A. The buttress 164 may, for example, be a separately molded structure onto which the remainder of the housing 102a is overmolded.

Figure 12:
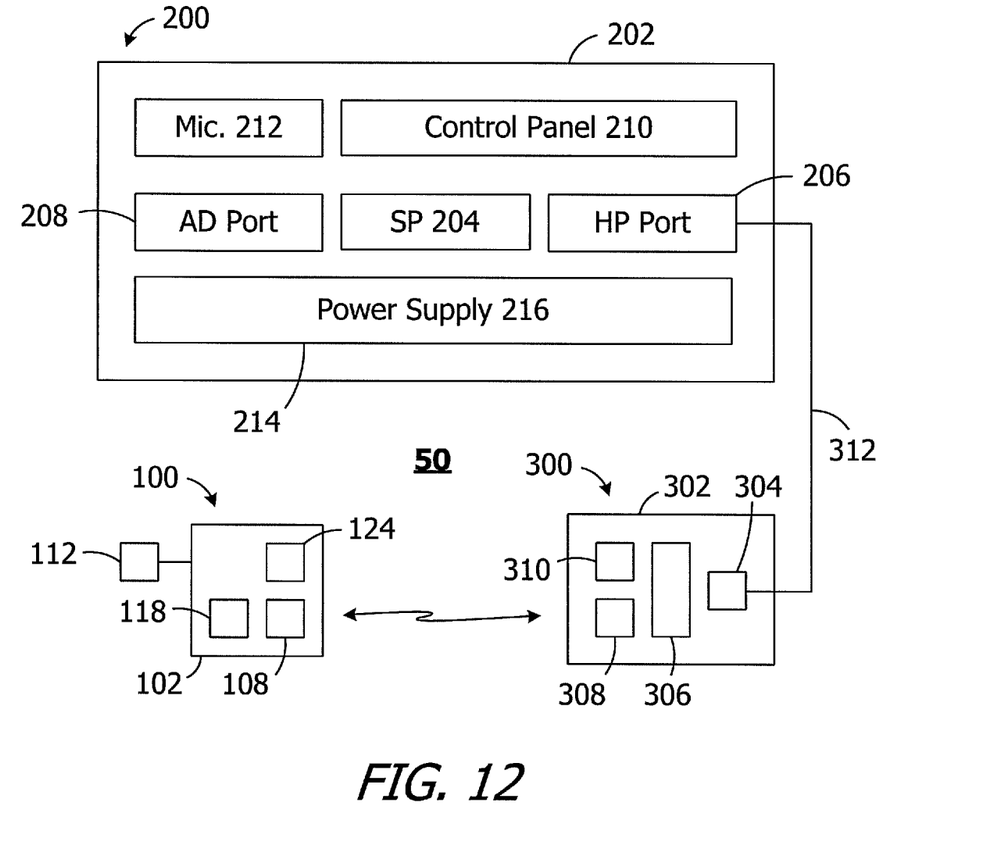
FIG. 12 is a block diagram of a cochlear implant system in accordance with one embodiment of a present invention.

As illustrated in FIG. 12, the exemplary cochlear implant system 50 includes the cochlear implant 100 (or 100a), a sound processor, such as the illustrated body worn sound processor 200 or a behind-the-ear sound processor, and a headpiece 300.

The exemplary body worn sound processor 200 in the exemplary ICS system 50 includes a housing 202 in which and/or on which various components are supported. Such components may include, but are not limited to, sound processor circuitry 204, a headpiece port 206, an auxiliary device port 208 for an auxiliary device such as a mobile phone or a music player, a control panel 210, one or microphones 212, and a power supply receptacle 214 for a removable battery or other removable power supply 216 (e.g., rechargeable and disposable batteries or other electrochemical cells). The sound processor circuitry 204 converts electrical signals from the microphone 212 into stimulation data. The exemplary headpiece 300 includes a housing 302 and various components, e.g., a RF connector 304, a microphone 306, an antenna (or other transmitter) 308 and a positioning magnet apparatus 310, that are carried by the housing. The magnet apparatus 310 may consist of a single magnet or may consist of one or more magnets and a shim. The headpiece 300 may be connected to the sound processor headpiece port 206 by a cable 312. The positioning magnet apparatus 310 is attracted to the magnet 124 of the cochlear stimulator 100, thereby aligning the antenna 308 with the antenna 108. The stimulation data and, in many instances power, is supplied to the headpiece 300. The headpiece 300 transcutaneously transmits the stimulation data, and in many instances power, to the cochlear implant 100 by way of a wireless link between the antennas. The stimulation processor 118 converts the stimulation data into stimulation signals that stimulate the electrodes 114 of the electrode array 112.

In at least some implementations, the cable 312 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 212 on the sound processor 200, the microphone 306 may be also be omitted in some instances. The functionality of the sound processor 200 and headpiece 300 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
a cochlear lead including a plurality of electrodes;
a flexible housing formed from a first flexible material having a first hardness and including a magnet pocket, a top wall above the magnet pocket, a bottom wall that does not include an opening below the magnet pocket, and a magnet aperture that extends through the top wall to the magnet pocket;
a magnet, located within the magnet pocket, having a top surface adjacent to the magnet aperture that defines a top magnet outer perimeter, a bottom surface adjacent to the bottom wall that defines a bottom magnet outer perimeter that is greater than the top magnet outer perimeter, and a side surface between the top surface and the bottom surface;
a flexible buttress located within the flexible housing adjacent to the side surface of the magnet, the flexible buttress being formed from a second flexible material having a second hardness that is greater than the first hardness;
an antenna within the flexible housing and adjacent to the magnet pocket; and
a stimulation processor within the flexible housing operably connected to the antenna and to the cochlear lead.

2. A cochlear implant as claimed in claim 1, wherein
the magnet defines a frustoconical shape; and
the flexible buttress has an inner surface that defines a frustoconical shape.

3. A cochlear implant, comprising:
a cochlear lead including a plurality of electrodes;
a flexible housing, formed from a first flexible material having a first hardness, including a magnet pocket, a top wall above the magnet pocket, a bottom wall that does not include an opening below the magnet pocket, and a magnet aperture that extends through the top wall to the magnet pocket;
a magnet, located within the magnet pocket, including a top surface adjacent to the magnet aperture, a bottom surface adjacent to the bottom wall, and a side surface between the top and bottom surfaces;
a flexible buttress located within the flexible housing and adjacent to the side surface of the magnet, the flexible buttress being formed from a second flexible material having a second hardness that is greater than the first hardness;
an antenna within the housing and adjacent to the magnet pocket; and
a stimulation processor within the housing operably connected to the antenna and to the cochlear lead.

4. A cochlear implant as claimed in claim 3, wherein the second flexible material is from 27% to 63% harder than the first material.

5. A cochlear implant as claimed in claim 3, wherein the first material has a hardness from 70 to 90 Shore A; the second flexible has a hardness from 55 to 70 Shore A.

6. A cochlear implant as claimed in claim 3, wherein
the top surface of the magnet defines a top magnet outer perimeter and the bottom surface of the magnet defines a bottom magnet outer perimeter that is greater than the top magnet outer perimeter; and
the flexible buttress has an inner surface with a top inner surface perimeter and a bottom inner surface perimeter that is greater than the top inner surface perimeter.

7. A cochlear implant as claimed in claim 3, wherein
the housing is formed from a first silicone elastomer; and
the buttress is formed from a second silicone elastomer that is harder than the first silicone elastomer.

* * * * *